United States Patent
Douglas et al.

Patent Number: 5,475,133
Date of Patent: Dec. 12, 1995

[54] BIS-PROPARGYL THERMOSETS

[75] Inventors: Elliot P. Douglas; David A. Langlois; Brian C. Benicewicz, all of Los Alamos, N.M.

[73] Assignee: The Regents of the University of California, Los Alamos, N.M.

[21] Appl. No.: 346,108

[22] Filed: Nov. 28, 1994

[51] Int. Cl.$^6$ .......................... C07C 69/76; C08F 38/00
[52] U.S. Cl. ............................... 560/61; 526/285
[58] Field of Search ................ 526/285; 560/61

[56] References Cited

U.S. PATENT DOCUMENTS

| | | |
|---|---|---|
| 3,816,374 | 6/1974 | White . |
| 4,226,800 | 10/1980 | Pickelsimer . |
| 4,567,240 | 1/1986 | Hergenrotter et al. ............ 526/285 |
| 4,885,403 | 12/1989 | Inbasekaran et al. . |
| 5,096,987 | 3/1992 | Pigneri . |
| 5,098,806 | 3/1992 | Robillard . |
| 5,114,612 | 5/1992 | Benicewicz et al. ............ 252/299.01 |
| 5,155,196 | 10/1992 | Kolb et al. . |
| 5,250,742 | 10/1993 | Kohleir et al. . |
| 5,315,011 | 5/1994 | Benicewicz et al. ............ 548/521 |

FOREIGN PATENT DOCUMENTS

| | | | |
|---|---|---|---|
| 398026 | 4/1991 | Japan ........................ | 526/285 |
| 693092 | 4/1994 | Japan ........................ | 526/285 |

OTHER PUBLICATIONS

CA 111: 174725–p. 6.
CA 115: 15217–1991–p. 14.

*Primary Examiner*—Joseph L. Schofer
*Assistant Examiner*—N. Sarafim
*Attorney, Agent, or Firm*—William A. Eklund; Bruce H. Cottrell

[57] ABSTRACT

The present invention provides (1) curable bispropargyl-containing monomers represented by the formula: $B^1$—$A^1_m$—R—$A^2_n$—$B^2$ wherein R is a radical selected from the group consisting of 1,4-phenylene, 4,4'-biphenyl, 2,6-naphthalene, —$C_6H_4$—$CR^2$=$CR^2$—$C_6H_4$— wherein $R^2$ is H or $CH_3$, and the same where said groups contain one or more substituents selected from the group consisting of halo, nitro, lower alkyl, lower alkoxy, fluoroalkyl or fluoroalkoxy, $A^1$ and $A^2$ are selected from the group consisting of —$C_6H_4$—C(O)—O— and —$C_6H_4$—O—C(O)—, m and n are 0 or 1, m+n is 0, 1 or 2, and $B^1$ and $B^2$ are —$OCH_2$—C≡C—H, (2) thermoset compositions comprised of cured segments derived from monomers represented by the formula: $B^1$—$A^1_m$—R—$A^2_n$—$B^2$ as described above, and (3) curable blends of at least two of the monomers.

7 Claims, No Drawings

BIS-PROPARGYL THERMOSETS

FIELD OF THE INVENTION

The present invention relates to the field of curable bis-propargyl-endcapped monomers, curable liquid crystal bis-propargyl-endcapped monomers and to thermoset compositions prepared therefrom. This invention is the result of a contract with the Department of Energy (Contract No. W-7405-ENG-36).

BACKGROUND OF THE INVENTION

Liquid crystal polymers are recognized as having great potential for the development of new materials with exceptional physical and mechanical properties. In general, liquid crystal polymers consist of polymer chains containing anisotropic structural units (mesogenic groups) which may be incorporated into the polymer backbone, as pendent groups, or both. The mesogenic groups may be rod-like or disc-like in nature. Fibers, films, and molded plastics processed from the liquid crystalline state have shown outstanding properties.

Another desirable characteristic of such liquid crystalline polymers would be that they be thermosetting. Liquid crystal thermosetting polymers are known, e.g., the acrylic-terminated thermoset resins and precursors disclosed by Conciatorri et al. in U.S. Pat. Nos. 4,440,945, 4,452,993, and 4,514,553, the epoxy-terminated thermoset resins and precursors disclosed by Muller et al. in U.S. Pat. No. 4,764,581, the various difunctionally terminated materials disclosed by Dhein et al. in U.S. Pat. No. 4,762,901.

Other thermosetting resins utilizing end groups such as maleimide, nadimide, methyl nadimide, and acetylenic are described in various patents such as U.S. Pat. Nos. 4,225,497, 4,550,177, 4,739,030, 4,661,604, 4,684,714, 4,851,495, 4,851,501, 5,114,612, 5,198,551, and 5,315,011.

Bis- or di-propargyl containing materials are known. (See, e.g., U.S. Pat. No. 4,226,800 to Picklesimer, U.S. Pat. No. 5,096,987 to Pigneri, U.S. Pat. No. 5,250,742 to Kohler et al., U.S. Pat. No. 4,885,403 to Inbasekaren and U.S. Pat. No. 5,155,196 to Kolb et al.). However, no liquid crystalline materials including bis- or di-propargyl groups are described in these patents.

It is an object of this invention to provide curable materials containing bis-propargyl endcaps. It is another object of this invention to provide curable liquid crystal materials containing bis-propargyl endcaps.

Another object of this invention is to provide thermoset bis-propargyl linked compositions including thermoset liquid crystal bis-propargyl linked compositions.

SUMMARY OF THE INVENTION

To achieve the foregoing and other objects, and in accordance with the purposes of the present invention, as embodied and broadly described herein, the present invention provides a curable bispropargyl-containing monomer represented by the formula: $B^1$—$A^1_m$—R—$A^2_n$—$B^2$ wherein R is a radical selected from the group consisting of 1,4-phenylene, 4,4'-biphenyl, 2,6-naphthalene, —$C_6H_4$—$CR^2$=$CR^2$—$C_6H_4$— wherein $R^2$ is H or $CH_3$, and the same where said groups contain one or more substituents selected from the group consisting of halo, nitro, lower alkyl/lower alkoxy, fluoroalkyl or fluoroalkoxy, $A^1$ and $A^2$ are selected from the group consisting of —$C_6H_4$—C(O)—O— and —$C_6H_4$—O—C(O)—, m and n are 0 or 1, m+n is 0, 1 or 2, and $B^1$ and $B^2$ are —$OCH_2$—C≡C—H.

The present invention further provides a thermoset composition comprised of cured segments derived from one or more monomers represented by the formula: $B^1$—$A^1_m$—R—$A^2_n$—$B^2$ wherein R is a radical selected from the group consisting of 1,4-phenylene, 4,4'-biphenyl, 2,6-naphthalene, —$C_6H_4$—$CR^2$=$CR^2$—$C_6H_4$— wherein $R^2$ is H or $CH_3$, and the same where said groups contain one or more substituents selected from the group consisting of halo, nitro, lower alkyl, lower alkoxy, fluoroalkyl or fluoroalkoxy, $A^1$ and $A^2$ are selected from the group consisting of —$C_6H_4$—C(O)—O— and —$C_6H_4$—O—C(O)—, m and n are 0 or 1, m+n is 0, 1 or 2, and $B^1$ and $B^2$ are —$OCH_2$—C≡C—H.

The present invention also provides curable blends including at least two monomers represented by the formula: $B^1$—$A^1_m$—R—$A^2_n$—$B^2$ wherein R is a radical selected from the group consisting of 1,4-phenylene, 4,4'-biphenyl, 2,6-naphthalene, —$C_6H_4$—$CR^2$=$CR^2$—$C_6H_4$— wherein $R^2$ is H or $CH_3$, and the same where said groups contain one or more substituents selected from the group consisting of halo, nitro, lower alkyl, lower alkoxy fluoroalkyl or fluoroalkoxy, $A^1$ and $A^2$ are selected from the group consisting of —$C_6H_4$—C(O)—O— and —$C_6H_4$—O—C(O)—, m and n are 0 or 1, m+n is 0, 1 or 2, and $B^1$ and $B^2$ are —$OCH_2$—C≡C—H.

The present invention also provides a curable blend including at least one monomer represented by the formula: $B^1$—$A^1_m$—R—$A^2_n$—$B^2$ wherein R is a radical selected from the group consisting of 1,4-phenylene, 4,4'-biphenyl, 2,6-naphthalene, —$C_6H_4$—$CR^2$=$CR^2$—$C_6H_4$— wherein $R^2$ is H or $CH_3$, and the same where said groups contain one or more substituents selected from the group consisting of halo, nitro, lower alkyl, lower alkoxy, fluoroalkyl or fluoroalkoxy, $A^1$ and $A^2$ are selected from the group consisting of —$C_6H_4$—C(O)—O— and —$C_6H_4$—O—C(O)—, m and n are 0 or 1, m+n is 0, 1 or 2, and $B^1$ and $B^2$ are —$OCH_2$—C≡C—H, and a curing agent.

The present invention also provides a process of preparing a curable monomer represented by the formula: $B^1$—$A^1_m$—R—$A^2_n$—$B^2$ wherein R is a radical selected from the group consisting of 1,4-phenylene, 4,4'-biphenyl, 2,6-naphthalene, —$C_6H_4$—$CR^2$=$CR^2$—$C_6H_4$— wherein $R^2$ is H or $CH_3$, and the same where said groups contain one or more substituents selected from the group consisting of halo, nitro, lower alkyl, lower alkoxy, fluoroalkyl or fluoroalkoxy, $A^1$ and $A^2$ are selected from the group consisting of —$C_6H_4$—C(O)—O— and —$C_6H_4$—O—C(O)—, m and n are 0 or 1, m+n is 0, 1 or 2, and $B^1$ and $B^2$ are —$OCH_2$—C≡C—H, said process including: reacting a dihydroxyaromatic compound with reactants selected from the group consisting of (1) two equivalents of a propargyl group containing acid; (2) two equivalents of a propargyl group containing acid chloride; (3) one equivalent of a propargyl group containing acid followed by one equivalent of propargyl chloride; (4) one equivalent of a propargyl group containing acid chloride followed by one equivalent of propargyl chloride; (5) two equivalents of propargyl chloride; (6) one equivalent of propargyl chloride followed by one equivalent of a propargyl group containing acid; and (7) one equivalent of propargyl chloride followed by one equivalent of a propargyl group containing acid chloride.

DETAILED DESCRIPTION

The present invention is concerned with curable or thermosettable monomers including curable or thermosettable liquid crystalline monomers represented by the formula: $B^1—A^1_m—R—A^2_n—B^2$ wherein R is a radical selected from the group consisting of 1,4-phenylene, 4,4'-biphenyl, 2,6-naphthalene, $—C_6H_4—CR^2=CR^2—C_6H_4—$ wherein $R^2$ is H or $CH_3$, and the same where said groups contain one or more substituents selected from the group consisting of halo, nitro, lower alkyl, lower alkoxy, fluoroalkyl or fluoroalkoxy, $A^1$ and $A^2$ are selected from the group consisting of $—C_6H_4—C(O)—O—$ and $—C_6H_4—O—C(O)—$, m and n are 0 or 1, m+n is 0, 1 or 2, and $B^1$ and $B^2$ are $—OCH_2—C{\equiv}C—H$. By the term "liquid crystalline" is meant that when a material is in the fluid state it exhibits some degree of molecular order, i.e., an order intermediate between a crystalline solid and an isotropic liquid.

Such curable monomers can be prepared by a process including: (1) reacting a dihydroxyaromatic compound with two equivalents of a propargyl group containing-acid or acid chloride; (2) reacting a dihydroxyaromatic compound with two equivalents of propargyl chloride; (3) reacting a dihydroxyaromatic with one equivalent of a propargyl group containing- acid or acid chloride followed by reaction with one equivalent of propargyl chloride; or (4) reaction a dihydroxyaromatic with one equivalent of propargyl chloride followed by reaction with one equivalent of a propargyl group containing acid or acid chloride.

Curable blends of the bis-propargyl endcapped monomers including blends with one or more bis-propargyl endcapped monomers are also provided by this invention. Such blends can allow the tailoring of properties such as melting points which may lower the processing temperatures of these materials. For example, by blending two or more of the monomers, the melting point of the blend can be depressed beneath that of the individual monomers. Where one or more of the blended monomers are liquid crystalline, the blend may retain the liquid crystallinity of that one or more monomer. The monomers are represented by the formula $B^1—A^1_m—R—A^2_n—B^2$ wherein R, $A^m$, $A^2$, m, n, $B^1$ and $B^2$ are as previously described.

The bis-propargyl endcapped monomers of this invention can be polymerized by heat alone, by the action of free radical initiators, by the addition of aromatic polyamines as bridging agents, by the presence of a catalytic amount of an alkali salt of a Bronsted acid, or by the addition of various metal catalysts such as bis(triphenylphosphine)palladium dichloride. Preferably, the monomers are polymerized by heat.

In addition to homopolymerization, the bis-propargyl endcapped monomers can be polymerized with various vinyl monomers such as styrene, acrylonitrile, acrylates and methacrylates, or with other type bis-propargyl endcapped monomers. Such copolymerizations can be initiated by free radical generating materials such as peroxides, azo compounds, etc. as well known to those skilled in the art of polymerization.

The endcapped monomers or compounds of the present invention can be used in prepregs or composites as is standard in the art. Crosslinking with the endcapped monomers generally can occur with heat alone upon heating the monomers to from about 150° C. to about 300° C., preferably from about 180° C. to about 250° C.

Prepregs of the endcapped monomers can be prepared by conventional techniques. While woven fabrics are the typical reinforcement, the fibers can be continuous or discontinuous, i.e., in chopped or whisker form, and may be ceramic, organic, glass or carbon, i.e., graphite, as is desired for the particular application.

Composites can be formed by curing the endcapped compounds or prepregs in conventional vacuum bag techniques. The endcapped compounds or monomers may also be used as adhesives, varnishes, films or coatings.

The present invention is more particularly described in the following examples which are intended as illustrative only, since numerous modifications and variations will be apparent to those skilled in the art. The examples A-D describe the preparation of starting materials used in subsequent examples.

EXAMPLE A

Methyl 4-hydroxybenzoate (50.00 grams (g) , 0.329 moles) was dissolved in 250 milliliters (ml) of dimetylacetamide. The solution was stirred as propargyl chloride (36.73 g, 0.493 moles) and potassium carbonate (68.14 g, 0.493 moles) were added to the reaction flask. The brown slurry was then allowed to stir at 90° C. for three hours. The reaction mixture was hot filtered and water (250 ml) was added to the dark orange filtrate. The filtrate was cooled and suction filtered, isolating beige crystals (99% yield) which were dried in a vacuum oven at 30° C. The product was used without further purification, but could be recystallized from acetone/water.

EXAMPLE B

Sodium hydroxide (13.16 g, 0.329 moles) was dissolved in a solution composed of 200 ml of water and 200 ml of methanol. Methyl 4-propargoxybenzoate from example A (50.00 g, 0.263 moles) was then added to the stirring solution, gradually dissolving. The orange solution was allowed to stir and reflux overnight. The solution was cooled to room temperature and then acidified with concentrated hydrochloric acid. The white product (97% yield) was isolated by suction filtration, washed with water and dried in a vacuum oven at 90° C.

EXAMPLE C

4-Propargoxybenzoic acid from example B (50.00 g, 0.284 moles) was suspended in 300 ml of benzene with stirring. Oxalyl chloride (90.12 g, 0.710 moles) was slowly added to the mixture resulting in gas evolution. The mixture was slowly heated to reflux and allowed to stir at reflux for three hours. The excess oxalyl chloride and approximately 30 percent of the benzene were removed by distillation. The remaining dark red solution was cooled resulting in the formation of crystals, after which hexane (300 ml) was added, and the solution heated to reflux. The solution was hot filtered, yielding a red filtrate which was cooled and suction filtered to isolate yellowish-tan crystals (76% yield) which were dried in a vacuum oven at 30° C.

EXAMPLE D

Hydroquinone (6.80 g, 0.0618 moles), 60 ml of anhydrous ether, and triethylamine (2.08 g, 0.0206 moles) were allowed to stir in an ice bath for thirty minutes. 4-Propargoxybenzoic acid (4.00 g, 0.0206 moles) was slowly added to the stirring mixture. The peach slurry was then allowed to stir at room temperature for three hours. Ether was removed from the reaction flask using a rotary evaporator and the remaining beige paste was stirred in 75 ml of warm water. Suction filtration isolated a tan solid which was dried in a vacuum oven at 50° C. The product was then purified using a chromatatron (25% ethyl acetate 75% hexane) and dried in a vacuum oven at 70° C.

EXAMPLE 1

Hydroquinone (also known as 1,4-dihydroxybenzene) (1.25 g, 0.0114 moles), 30 ml of anhydrous ether, and triethylamine (2.31 g, 0.0228 moles) were allowed to stir in an ice bath for thirty minutes. 4-Propargoxybenzoic acid (4.44 g, 0.0288 moles) was slowly added to the stirring mixture. The beige slurry was then allowed to stir at room temperature for three hours. Ether was removed from the reaction flask using a rotary evaporator and the remaining beige paste was stirred in 50 ml of warm water. Suction filtration isolated a beige solid which was dried in a vacuum oven at 50° C. The product was recrystallized from acetonitrile and dried in a vacuum oven at 80° C. The resultant compound shown as structure no. 1:

was heated in a polarized optical microscope (POM) from room temperature and exhibited a nematic texture at 171° C.

EXAMPLE 2

The procedure of example 1 was repeated with the exception that similar molar amounts of substituted 1,4-dihydroxybenzenes were used in place of the hydroquinione. The following table shows the particular substituted 1,4-dihydroxybenzene used, the solvent used for recrystallization and the results upon heating in a polarized optical microscope.

| name of substituted dihydroxybenzene | solvent for recrystallization | structure no.; POM results |
|---|---|---|
| 1,4-dihydroxy-2,3-dimethylbenzene | acetonitrile | no. 2; nematic texture at 161° C. |
| 2-chloro-1,4-dihydroxybenzene | acetonitrile/ dimethylformamide | no. 3; isotropic melt at 201° C. |
| 1,4-dihydroxy-2-phenylbenzene | acetonitrile | no. 4; isotropic melt at 109° C. |
| 1,4-dihydroxy-2-methylbenzene | acetonitrile | no. 5; nematic texture at 163° C. upon cooling in POM from 200° C. |
| 1,4-dihydroxy-2-methoxybenzene | isopropanol | no. 6; nematic texture at 115° C. upon cooling in POM from 200° C. |

The monomer of structure no. 2 is as follows:

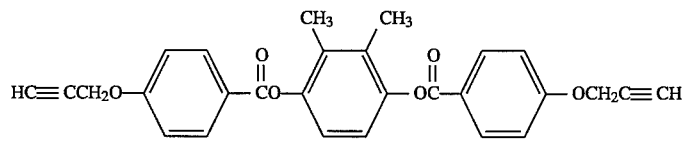

The monomer of structure no. 3 is as follows:

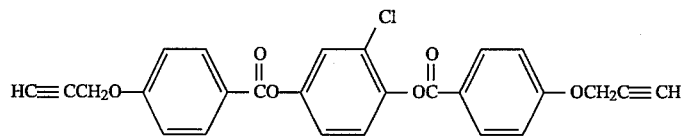

The monomer of structure no. 4 is as follows:

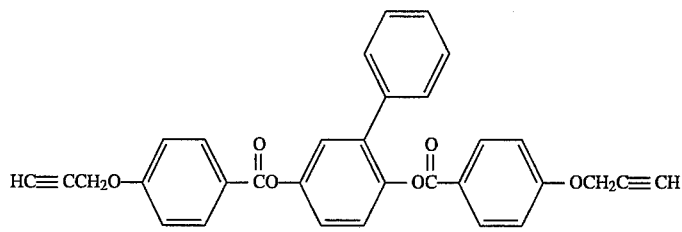

The monomer of structure no. 5 is as follows:

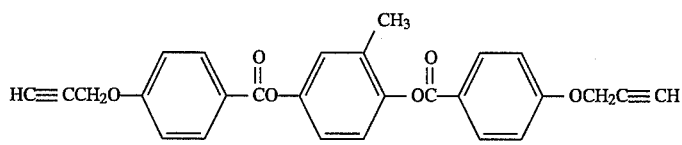

The monomer of structure no. 6 is as follows:

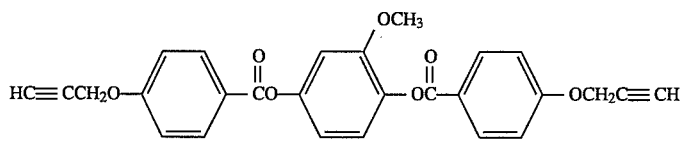

The monomers of structures nos. 5 and 6 also formed a liquid crystalline phase upon subsequent heating following an initial B-staging, i.e., partial curing by heating for a short time at a temperature of, e.g., 215° C.

EXAMPLE 3

The procedure of example 1 was repeated with the exception that similar molar amounts of other dihydroxy compounds were used in place of the hydroquinione. The following table shows the particular dihydroxy compound used, the solvent used for recrystallization and the results upon heating in a polarized optical microscope.

| name of dihydroxy compound | solvent for recrystallization | structure no.; POM results |
|---|---|---|
| 2,6-dihydroxy-naphthalene | dimethylformamide/water | no. 7; nematic texture at 215° C. |
| 4,4'-dihydroxybiphenyl | dimethylformamide/water | no. 8; nematic texture at 192° C. |
| 4,4'-dihydroxy-2,2'-dimethylbiphenyl | acetone/water | no. 9; nematic texture at 136° C. |

The monomer of structure no. 7 is as follows:

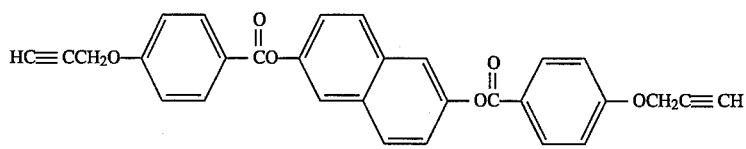

The monomer of structure no. 8 is as follows:

no. 11:

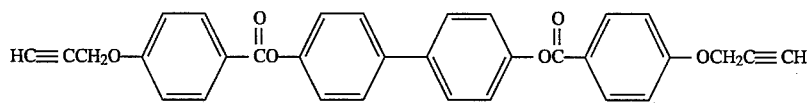

The monomer of structure no. 9 is as follows:

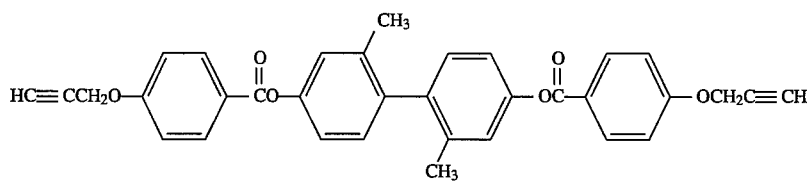

EXAMPLE 4

4-Hydroxyphenyl-4-propargoxybenzoate from example D (1.25 g, 0.00466 moles) was dissolved in 10 ml of dimethylacetamide. The solution was stirred as propargyl chloride (0.52 g, 0.00699 moles) and potassium carbonate (0.97 g, 0.00699 moles) were added to the reaction flask. The brown slurry was then allowed to stir at 90° C. for three hours. The reaction mixture was hot filtered and water (10 ml) was added to the filtrate. The filtrate was then cooled and centrifuged with the tan solution being decanted off the product. The product was washed twice with water and then dried in a vacuum oven at 60° C. The resultant compound shown as structure no. 10:

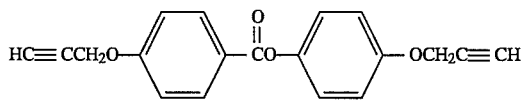

was heated in a polarized optical microscope from room temperature and exhibited an isotropic melt at 124° C.

EXAMPLE 5

4,4'-dihydroxystilbene (1.25 g, 0.00589 moles) was stirred in 25 ml of dimethylacetamide as propargyl chloride (1.32 g, 0.01767 moles) and potassium carbonate (2.44 g, 0.01767 moles) were added to the reaction flask. The brown slurry was then allowed to stir at 90° C. for three hours. The reaction mixture was hot filtered and water (25 ml) was added to the amber filtrate. The filtrate was then cooled and suction filtered to isolate tan crystals. The product was recystallized using acetone/water and then dried in a vacuum oven at 40° C. The resultant compound, shown as structure

HC≡CCH₂O—⟨⟩—CH=CH—⟨⟩—OCH₂C≡CH was heated in a polarized optical microscope from room temperature and exhibited an isotropic melt at 200° C.

EXAMPLE 6

The procedure of example 1 was repeated with the exception that similar molar amounts of stilbene and substituted stilbene compounds were used in place of the hydroquinone. The following table shows the particular dihydroxy compound used, the solvent used for recrystallization and the results upon heating in a polarized optical microscope.

| name of stilbene or substituted 1,4-dihydroxystilbene | solvent for recrystallization | structure no.; POM results |
| --- | --- | --- |
| stilbene | dimethylformamide/water | no. 12; nematic texture at 208° C. |
| dihydroxy-alphamethyl-stilbene | acetonitrile/formamide | no. 13; nematic texture at 170° C. |
| 3,3'dimethyl-4,4'-dihydroxystilbene | acetonitrile/dimethylformamide | no. 14; nematic texture at 208° C. |

The monomer of structure no. 12 is as follows:

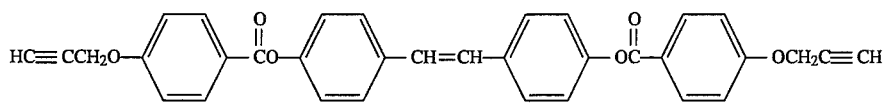

The monomer of structure no. 13 is as follows:

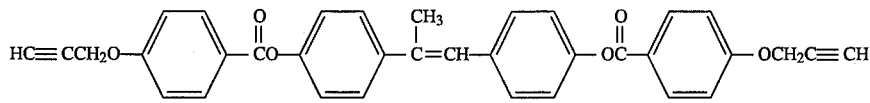

The monomer of structure no. 14 is as follows:

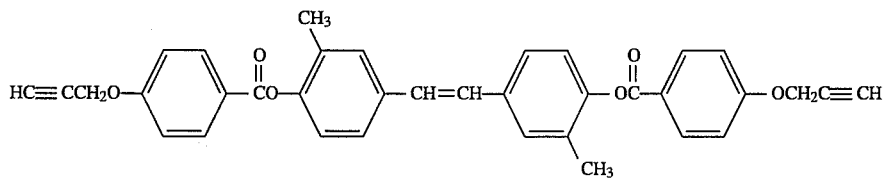

Although the present invention has been described with reference to specific details, it is not intended that such details should be regarded as limitations upon the scope of the invention, except as and to the extent that they are included in the accompanying claims.

What is claimed is:

1. A curable bispropargyl-containing monomer represented by the formula: $B^1$—$A^1{}_m$—R—$A^2{}_n$—$B^2$ wherein R is a radical selected from the group consisting of 1,4-phenylene, 4,4'-biphenyl, 2,6-naphthalene, —$C_6H_4$—$CR^2$=$CR^2$—$C_6H_4$— wherein $R^2$ is H or $CH_3$, and the same where said radical contains one or more substituents selected from the group consisting of halo, nitro, lower alkyl, lower alkoxy, fluoroalkyl or fluoroalkoxy, $A^1$ and $A^2$ are selected from the group consisting of —$C_6H_4$—C(O)—O— and —$C_6H_4$—O—C(O)—, m and n are 0 or 1, m+n is 0, 1 or 2 and $B^1$ and $B^2$ are —$OCH_2$—C≡C—H.

2. The curable bispropargyl-containing monomer of claim 1 wherein R is 1,4-phenylene and the same where said radical contains one or more substituents selected from the group consisting of halo, nitro, lower alkyl, lower alkoxy, fluoroalkyl or fluoroalkoxy, and m and n are 1.

3. The curable bispropargyl-containing monomer of claim 1 wherein R is 4,4'-biphenyl, and the same where said radical contains one or more substituents selected from the group consisting of halo, nitro, lower alkyl, lower alkoxy, fluoroalkyl or fluoroalkoxy, and m and n are 1.

4. The curable bispropargyl-containing monomer of claim 1 wherein R is 2,6-naphthalene and the same where said radical contains one or more substituents selected from the group consisting of halo, nitro, lower alkyl, lower alkoxy, fluoroalkyl or fluoroalkoxy, and m and n are 1.

5. The curable bispropargyl-containing monomer of claim 1 wherein R is —$C_6H_4$—$CR^2$=$CR^2$—$C_6H_4$— wherein $R^2$ is H or $CH_3$, and the same where said radical contains one or more substituents selected from the group consisting of halo, nitro, lower alkyl, lower alkoxy, fluoroalkyl or fluoroalkoxy, and m and n are 0 or 1.

6. The curable bispropargyl-containing monomer of claim 1 wherein R is 1,4-phenylene and the same where said radical contains one or more substituents selected from the group consisting of halo, nitro, lower alkyl, lower alkoxy, fluoroalkyl or fluoroalkoxy, m is 0 and n is 1.

7. The curable bispropargyl-containing monomer of claim 1 wherein R is —$C_6H_4$—$CR^2$=$CR^2$—$C_6H_4$— wherein $R^2$ is H or $CH_3$, and the same where said radical contains one or more substituents selected from the group consisting of halo, nitro, lower alkyl, lower alkoxy, fluoroalkyl or fluoroalkoxy, m and n are 0.

* * * * *